United States Patent [19]

Auclair

[11] 4,321,260
[45] Mar. 23, 1982

[54] METHOD OF USING GONADORELIN FOR THE TREATMENT OF BENIGN PROSTATIC HYPERPLASIA

[75] Inventor: Claude Auclair, Soulanges, Canada

[73] Assignee: Ayerst, McKenna & Harrison Inc., Montreal, Canada

[21] Appl. No.: 152,241

[22] Filed: May 22, 1980

[51] Int. Cl.³ .................... A61K 37/00; C07C 103/52
[52] U.S. Cl. ........................... 424/177; 260/112.5 LH
[58] Field of Search ............... 260/112.5 LH; 424/177

[56] References Cited

PUBLICATIONS

A. V. Schally, et al., Am. J. Obstetrics and Gynecology, 114 (1972).
Chem. Abstr. vol. 73, 1970, p. 107506d.
Chem. Abstr. vol. 82, 1975, p. 119295h.
Chem. Abstr. vol. 93, 1980, p. 1242n.
Chem. Abstr. vol. 84, 1976, p. 145684v.

*Primary Examiner*—Delbert R. Phillips
*Attorney, Agent, or Firm*—Adley F. Mandel

[57] ABSTRACT

Herein is described a method of treating benign prostatic hyperlasia without affecting testicular weight in a male mammal by administering an effective amount of gonadorelin.

3 Claims, No Drawings

METHOD OF USING GONADORELIN FOR THE TREATMENT OF BENIGN PROSTATIC HYPERPLASIA

BACKGROUND OF THE INVENTION

This invention relates to a new method of using gonadorelin. This decapeptide is useful for treating benign prostatic hyperplasia without affecting testicular weight. Gonadorelin is the generic name for luteinizing hormone-releasing factor (LH-RH) having the chemical structure, Pyr-His-Trp-Ser-Tyr-Gly-Leu-Arg-Pro-Gly-NH$_2$.

The structure of gonadorelin is well known and a number of synthesis of the decapeptide are reported, for example, see H. U. Immer et al., U.S. Pat. No. 3,835,108, issued Sept. 10, 1974, incorporated herein by reference. Although numerous medical uses of gonadorelin have been reported, this invention describes a new use of the decapeptide for treating benign prostatic hyperplasia.

A few nonapeptide derivatives of gonadorelin have been reported to be effective for treating various tumors, for example, E. S. Johnson and J. H. Seely, U.S. Pat. No. 4,002,738, issue Jan. 11, 1977; E. S. Johnson and J. H. Seely, U.S. Pat. No. 4,071,622, issued Jan. 31, 1978 and E. S. Johnson, U.S. Pat. No. 4,005,194, issued Jan. 25, 1977. The first two U.S. patents relate to method of reducing the size of mammary and 7,12-dimethylbenzanthracene tumors by administering certain nonapeptides. The third U.S. patent, U.S. Pat. No. 4,005,194, describes nonapeptide derivatives which are effective for treating prostatic hyperplasia, some of these nonapeptides have an undesirable side effect wherein a marked reduction of the testicular weight is also observed, C. Auclair et al., Endocrinology, 101, 1890 (1977) and C. Auclair et al., Biochem. Biophys. Res. Commun., 76, 855 (1977).

SUMMARY OF THE INVENTION

Herein is described a method of reducing or preventing undesirable prostatic growth in a male mammal by administering to the mammal an effective amount of a decapeptide of the formula Pyr-His-Trp-Ser-Tyr-Gly-Leu-Arg-Pro-Gly-NH$_2$ to reduce or prevent prostatic growth. This method is especially useful for the treatment of benign prostatic hyperplasia.

DETAILS OF THE INVENTION

In general the abbreviations used herein for designating the amino acids are based on recommendations of the IUPAC-IUB Commission on Biochemical Nomenclature, see Biochemistry, 11, 1726-1732 (1972). For instance, Pyr, His, Trp, Ser, Tyr, Leu, Arg, Pro and Gly represent the "residues" of 5-oxo-L-proline, L-histidine, L-tryptophan, L-serine, L-tyrosine, L-leucine, L-arginine, L-proline and glycine respectively. The term "residue" refers to a radical derived from the corresponding α-amino acid by eliminating the hydroxyl of the carboxy group and one hydrogen of the α-amino group.

For reducing or preventing excess prostatic growth in a male mammal, gonadorelin is administered to the mammal at a parenteral dose in the range of about 0.035 mg to 11.0 mg per kilogram of body weight per day. A preferred parenteral dose is in the range of about 0.080 mg to 2.0 mg per kilogram of body weight per day. Gonadorelin can be parenterally administered to the mammal by intravenous injection or subcutaneous injection, preferably subcutaneously. A preferred vehicle in which to administer it is physiological saline with or without 1% gelatin. Other suitable parenteral compositions of gonadorelin are described in the above cited U.S. Pat. No. 3,835,108.

Daily administration of gonadorelin induces a significant decrease of the weight of the seminal vesicle and ventral prostate without affecting testicular weight. Thus, gonadorelin is useful for treating benign prostatic hyperplasia at a dose which does not affect testicular weight.

The following example illustrates further this invention.

ANIMALS

Adult male Sprague-Dawley rats weighing 275–325 g upon arrival were obtained from Canadian Breeding Laboratories, St. Constant, Quebec, Canada. All animals were housed 2 per cage in an air-conditioned (21±1° C.; 45–50% humidity) and light (12 hours light, 12 hours darkness)-controlled room and given food and water ad libitum.

TREATMENTS

Groups of rats (10 per group) were injected subcutaneously daily for 3 consecutive weeks with gonadorelin hydrochloride in a vehicle of saline containing 1% (v/v) of gelatin, (0.2 ml) or the vehicle alone. Rats were killed by decapitation 24 hours after the last injection. The testes, seminal vesicles and ventral prostate were removed, chilled, weighed and kept frozen at −20° C. until use.

RESULTS

Weights of the seminal vesicles and ventral prostate from the control and treated animals are given in Table 1. Weights of the testes from the control and treated animals are given in Table 2.

TABLE 1.

Effect of a 3-week treatment with increasing doses of gonadorelin (LH-RH) on the weight of the seminal vesicles and ventral prostate. Organ weights are expressed in mg of wet weight. Rats were injected s.c. daily with the indicated dose of gonadorelin

| Organ | TREATMENT | WEEKS OF TREATMENT | | | |
|---|---|---|---|---|---|
| | | 0 | 1 | 2 | 3 |
| Seminal Vesicles (mg) | Control | 295±10 | 305±10 | 354±10 | 353±16 |
| | LH-RH 25µg | | 281±14 | 247±9** | 260±13** |
| | LH-RH 250µg | | 298±10 | 249±18** | 210±8** |
| | LH-RH 2500µg | | 265±10* | 236±13** | 225±9** |
| Ventral Prostate (mg) | Control | 342±25 | 394±24 | 490± | 490±31 |
| | LH-RH 25µg | | 359±23 | 415±31* | 378±13** |
| | LH-RH 250µg | | 360±26 | 380±38** | 370±25** |
| | LH-RH 2500µg | | 325±12* | 355±31** | 373±18** |

*P<0.05 experimental vs control of the same week.
**P<0.01 experimental vs control of the same week.

TABLE 2.

Effect of a 3-week treatment with increasing doses of gonadorelin (LH-RH) on the weight of the testes. Organ weights are expressed in g of wet weight. Rats were injected s.c. daily with the indicated dose of gonadorelin.

| Organ | TREATMENT | WEEKS OF TREATMENT | | | |
|---|---|---|---|---|---|
| | | 0 | 1 | 2 | 3 |
| Testes (g) | Control | 2.99 ± 0.09 | 2.81 ± 0.14 | 3.16 ± 0.10 | 3.14 ± 0.14 |
| | LH-RH 25µg | | 2.79 ± 0.12 | 3.06 ± 0.05 | 3.11 ± 0.14 |
| | LH-RH 250 µg | | 3.01 ± 0.08 | 2.88 ± 0.14 | 3.17 ± 0.10 |
| | LH-RH 2500µg | | 2.75 ± 0.12 | 2.65 ± 0.09** | 2.74 ± 0.10** |

**$P<0.01$ experimental vs control of the same week.

Tables 1 and 2 show that daily subcutaneous administration to male rats of gonadorelin up to three weeks significantly decreases the weight of seminal vesicles and ventral prostate weight while not affecting the testicular weight of the animals. Daily doses of 25 µg and 250 µg (i.e. 0.08 mg and 0.8 mg per kilogram of body weight) are particularly effective in showing this selective effect. The selective effect is surprising in view of the reports that potent analogs of LH-RH such as [D-Ala$^6$, des-Gly-NH$_2$$^{10}$]-LH-RH ethylamide and [D-Leu$^6$, des-Gly-NH$_2$$^{10}$]-LH-RH ethylamide, reported in U.S. Pat. No. 4,005,194, noted above, do not show such a selectivity, see L. Cusan et al., Endocrinology, 104, 1369 (1979) and C. Auclair et al., Endocrinology, 101, 1890 (1977).

Accordingly, the results obtained with gonadorelin demonstrate clearly that gonadorelin can be used for treating prostatic hypertropy without a deleterious effect on the testes.

I claim:

1. A method of reducing or preventing the undesirable prostatic growth of benign prostatic hyperplasia in a male mammal without affecting testicular growth which comprises parenterally administering to said mammal about 0.035 mg to 9.0 mg per kilogram of body weight per day of a decapeptide of the formula Pyr-His-Trp-Ser-Tyr-Gly-Leu-Arg-Pro-Gly-NH$_2$ to reduce or prevent said prostatic growth.

2. A method of claim 1 wherein said decapeptide is administered at a parenteral dose of about 0.080 mg to 2.0 mg per kilogram of body weight per day.

3. A method of claim 1 wherein said decapeptide is administered at a parenteral dose of about 0.080 mg to 0.80 mg per kilogram of body weight per day.

* * * * *